United States Patent
Heid

(10) Patent No.: US 9,220,918 B2
(45) Date of Patent: Dec. 29, 2015

(54) MEDICAL DEVICE OPERATING WITH X-RAYS AND METHOD FOR OPERATING SAME

(75) Inventor: Oliver Heid, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 207 days.

(21) Appl. No.: 13/579,921

(22) PCT Filed: Feb. 2, 2011

(86) PCT No.: PCT/EP2011/051459
§ 371 (c)(1),
(2), (4) Date: Aug. 17, 2012

(87) PCT Pub. No.: WO2011/104075
PCT Pub. Date: Sep. 1, 2011

(65) Prior Publication Data
US 2012/0314841 A1    Dec. 13, 2012

(30) Foreign Application Priority Data

Feb. 24, 2010    (DE) .......................... 10 2010 009 019

(51) Int. Cl.
*A61N 5/10*    (2006.01)
*A61B 6/03*    (2006.01)
(Continued)

(52) U.S. Cl.
CPC . *A61N 5/10* (2013.01); *A61B 6/032* (2013.01); *A61B 6/4035* (2013.01); *A61B 6/542* (2013.01); *A61N 5/1081* (2013.01); *A61N 5/01* (2013.01)

(58) Field of Classification Search
CPC ......... A61N 5/01; A61N 5/10; A61N 5/1042; A61N 5/1049; A61N 5/1081; A61N 2005/1061; A61B 6/032; A61B 6/035; A61B 6/542; A61B 6/1081; A61B 6/4035
USPC ........... 378/11, 14, 16, 64, 65, 126, 150, 151, 378/156, 160; 3/11, 14, 16, 64, 65, 126, 3/150, 151, 156, 160
See application file for complete search history.

(56) References Cited

U.S. PATENT DOCUMENTS

| 3,973,128 A | 8/1976 | LeMay | ............................ 378/19 |
| 4,010,370 A | 3/1977 | LeMay | ............................ 378/12 |

(Continued)

FOREIGN PATENT DOCUMENTS

| CN | 101927063 A | 12/2010 | ............... A61N 5/10 |
| DE | 2439847 A1 | 4/1975 | ............... A61B 6/00 |

(Continued)

OTHER PUBLICATIONS

Miracle et al., Conebeam CT of the Head and Neck, Part 1: Physical Principles, Jun.-Jul., 2009, Am. J. Neuroradiol. vol. 30, p. 1091.*
(Continued)

*Primary Examiner* — David J Makiya
*Assistant Examiner* — Julio M Duarte-Carvajalino
(74) *Attorney, Agent, or Firm* — Slayden Grubert Beard PLLC

(57) ABSTRACT

The invention relates to a medical device operating with X-rays, comprising: an X-ray source, from which an X-ray beam that has an intensity maximum along a central ray can be emitted, a rotation unit, with which the X-ray source can be rotated about an isocenter, wherein the central axis of the X-ray beam is oriented eccentrically to the isocenter such that, in particular upon rotation about the isocenter, the central rays emitted from different spatial directions are tangential to an imaginary circle around the isocenter. Furthermore, the invention relates to a method for operating a medical device, comprising the following steps: providing an X-ray source, from which an X-ray beam that has an intensity maximum along a central ray is emitted, rotating the X-ray source about an isocenter.

7 Claims, 1 Drawing Sheet

(51) Int. Cl.
*A61B 6/00* (2006.01)
*A61N 5/01* (2006.01)

(56) References Cited

U.S. PATENT DOCUMENTS

| | | | |
|---|---|---|---|
| 4,304,999 A | 12/1981 | Richey et al. | 378/4 |
| 2003/0021385 A1 | 1/2003 | Izuhara | 378/195 |
| 2005/0089141 A1 | 4/2005 | Brown | 378/65 |
| 2006/0153330 A1* | 7/2006 | Wong et al. | 378/65 |
| 2008/0021300 A1* | 1/2008 | Allison | 600/407 |
| 2008/0298550 A1* | 12/2008 | Otto | 378/65 |
| 2009/0080603 A1 | 3/2009 | Shukla et al. | 378/65 |
| 2009/0252292 A1* | 10/2009 | Simon et al. | 378/25 |
| 2012/0314841 A1 | 12/2012 | Heid | 378/65 |

FOREIGN PATENT DOCUMENTS

| | | | | |
|---|---|---|---|---|
| DE | 2551322 A1 | 5/1976 | | A61B 6/03 |
| DE | 7520713 U | 1/1978 | | A61B 6/02 |
| EP | 1419799 A1 | 5/2004 | | A61B 16/00 |
| JP | 6131175 A | 2/1986 | | A61N 5/10 |
| WO | 00/74779 A1 | 12/2000 | | A61N 5/01 |
| WO | 2005/053794 A1 | 6/2005 | | A61B 6/00 |
| WO | 2011/104075 A1 | 9/2011 | | A61N 5/10 |

OTHER PUBLICATIONS

Pla, Marina et al., "Total Body Irradiation with a Sweeping Beam," Int. J. of Radiation Oncology Biol. Phys., vol. 9(1), 7 pages, Jan. 1983.

Kobayahski, Hidetoshi et al., "Computer-Assisted Conformation Radiotherapy with a Variable Thickness Multi-Leaf Filter," Int. J. of Radiation Oncology Biol. Phys., vol. 16(6), 5 pages, Jun. 1989.

International Search Report and Written Opinion, Application No. PCT/EP2011/051459, 22 pages, May 3, 2011.

Chinese Office Action, Application No. 201180011150.7, 7 pages, Jun. 4, 2014.

* cited by examiner

MEDICAL DEVICE OPERATING WITH X-RAYS AND METHOD FOR OPERATING SAME

CROSS-REFERENCE TO RELATED APPLICATIONS

This application is a U.S. National Stage Application of International Application No. PCT/EP2011/051459 filed Feb. 2, 2011, which designates the United States of America, and claims priority to DE Patent Application No. 10 2010 009 019.0 filed Feb. 24, 2010. The contents of which are hereby incorporated by reference in their entirety.

TECHNICAL FIELD

This disclosure relates to a medical device operating with x-rays, in particular a radiation therapy device, as well as method for operating the same.

BACKGROUND

The irradiation of a finite target volume by means of x-rays from different spatial directions, such as is implemented for instance for the purposes of imaging in diagnostic methods or dose synthesis in therapeutic methods, usually requires as homogenous a gross illumination of the target volume as possible.

Since the x-ray sources usually have a preferred beam direction, along which the maximum dose is located, and the beam direction is usually aligned toward the center of the target volume, the illumination of the boundary areas of the target volume is usually reduced compared with the center of the target volume.

The problem with radiation therapy devices and with imaging devices was previously solved by a beam flattening filter, which flattens the central portions of the radiation lobe and thus homogenizes the profile of the x-ray beam.

SUMMARY

In one embodiment, a medical device operating with x-rays may comprise: an x-ray radiation source, with which an x-ray radiation cone can be emitted, which has a maximum intensity along a central beam, and a rotation apparatus, with which the x-ray radiation source can be rotated about an isocenter, wherein the central axis of the x-ray radiation cone is aligned paraxially past the isocenter.

In a further embodiment, the central axis of the x-ray radiation cone is aligned paraxially past the isocenter such that upon rotation around the isocenter, the central beams emitted from different spatial directions are tangential to an imaginary circle around the isocenter. In a further embodiment, the device is embodied as a radiation therapy device. In a further embodiment, a collimator exists in the radiation path of the x-ray radiation cone for lateral delimitation of the beam profile of the x-ray beam. In a further embodiment, no beam flattening filter which is used for spatial dose homogenization is arranged in the radiation path of the x-ray radiation cone.

In another embodiment, a method for operating a medical device may comprise: providing an x-ray radiation source, with which an x-ray radiation cone is emitted, which has a maximum intensity along a central beam, and rotating the x-ray radiation source about an isocenter, wherein the central axis of the x-ray radiation cone is directed paraxially past the isocenter.

In a further embodiment, the central axis of the x-ray radiation cone is directed paraxially past the isocenter such that upon rotation around the isocenter, the central beams emitted from different spatial directions are tangential to an imaginary circle around the isocenter. In a further embodiment, no beam flattening filter used for spatial dose homogenization is arranged in the radiation path of the x-ray radiation cone. In a further embodiment, the x-ray radiation cone is collimated.

Another embodiment provides a use of an x-ray radiation cone, which has a maximum intensity along a central beam, which, with a medical device operating with x-rays, is emitted by an x-ray source from different spatial directions about an isocenter, for dose homogenization in an area around the isocenter, by the central beam of the x-ray radiation cone being aligned laterally past the isocenter in each spatial direction.

BRIEF DESCRIPTION OF THE DRAWINGS

Example embodiments will be explained in more detail below with reference to figures, in which.

DETAILED DESCRIPTION

Figure 1:
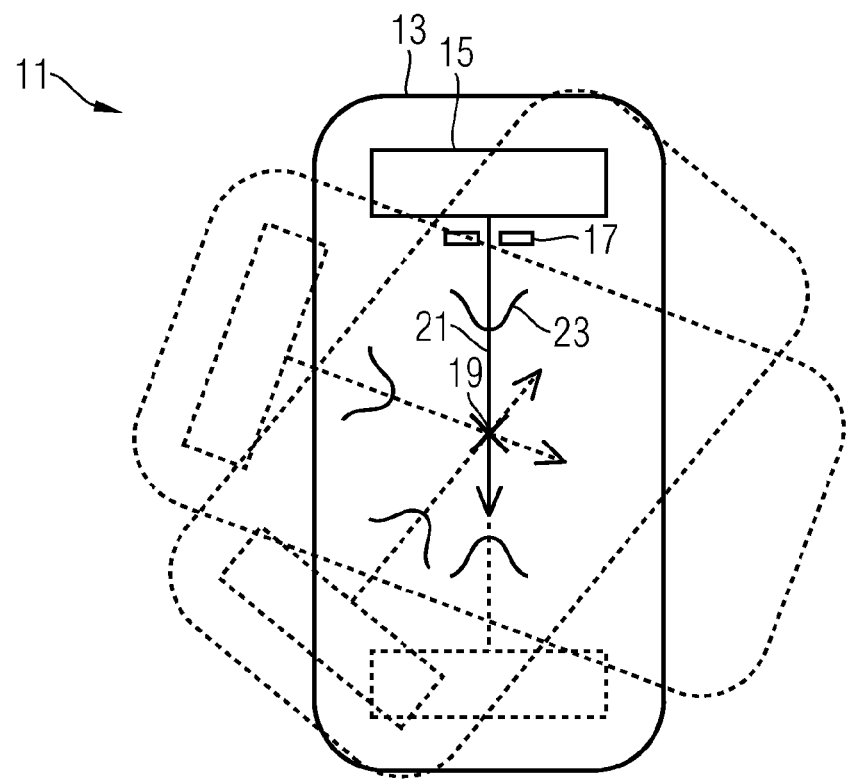
FIG. 1 shows the principle of dose generation in a radiation therapy device according to the prior art.

Some embodiments provide a medical device operating with x-rays, which enables a rapid and efficient illumination of a target volume. Furthermore, some embodiments provide a method with which it is possible to illuminate a target volume rapidly and efficiently.

Some embodiments provide a medical device operating with x-rays, which may include:
an x-ray radiation source, with which an x-ray can be emitted, which has a maximum dose along a central beam, and
a rotation apparatus, with which the x-ray radiation source can be rotated about an isocenter,
wherein the central axis of the x-ray beam is aligned eccentrically to the isocenter, so that in particular upon rotation around the isocenter, the central beams emitted from different spatial directions are tangential to an imaginary circle around the isocenter.

Certain embodiments are based on the knowledge that the radiation lobe of an x-ray source, in other words the x-ray cone emitted by the x-ray source, usually has a maximum along the central beam. The radiation lobe of the x-ray source is now no longer directed at the center, but instead more at the boundary area. The irradiation therefore takes place paraxially and/or tangentially from different spatial directions.

By rotating the source around the target volume, a significantly more homogenous illumination of the entire volume is achieved on the whole, even if the radiation lobe itself indicates an inhomogeneous dose profile. The more homogenous illumination is enabled by the combination of inhomogeneous dose profile of the radiation lobe, which flattens around a maximum dose along the central beam, an eccentric alignment of the radiation lobe and of the rotation of the radiation lobe.

The geometric arrangement and alignment of the x-ray source together with the rotation of the x-ray source therefore contribute to the homogenization of the illumination.

Compared with previous solutions, in which the homogenization is largely effected by an absorber, a significantly improved efficiency of the x-ray source can be achieved.

The absorber can namely be embodied such that it absorbs less radiation power, since it no longer has to cater for the homogenization of the dose profile on its own. It can even be completely omitted, so that the complete dose output of the source strikes the target volume. The latter case is free of beam flattening filters used for homogenization in the x-ray radiation path. Overall, it is therefore possible to dispense with a lossy, radiation-blasted absorber.

The dose rate with which a target volume can be illuminated increases as a result. The irradiation duration depends on the fraction (desired dose)/(local dose rate) formed across the tumor volume. The site to be irradiated at which the minimal dose rate occurs, in other words the least irradiated region, therefore defines the irradiation duration. Time can therefore be reduced using the medical device disclosed herein.

With an inhomogeneous dose distribution, it also applies that locations irradiated at the same time with higher dose rates are protected from the radiation for a part of the irradiation duration, since otherwise an excessively high dose would be applied there. A more homogenous dose distribution also solves this problem. Locations with an excessively high dose rate need not be masked out after a short period of time, e.g. with a collimator, so that the desired dose can be applied with a lower dose rate at another location.

In particular, the device can be embodied as a radiation therapy device, for instance with a therapeutic x-ray radiation source, which can be rotated about an isocenter.

A collimator can be present in the radiation path of the x-ray, with which the beam profile of the x-ray can then be laterally delimited and can thus be adjusted to a target volume to be irradiated for instance. Only certain partial volumes can therefore be irradiated with an object to be irradiated.

Some embodiments provide a method for operating a medical device, comprising:
  providing an x-ray radiation source, with which an x-ray beam is emitted, which has a maximum intensity along a central beam, and
  rotating the x-ray radiation source about an isocenter, wherein during rotation the central axis of the x-ray beam is aligned eccentrically to the isocenter such that in particular upon rotation about the isocenter, the central beams emitted from different directions are tangential to an imaginary circle around the isocenter.

In some embodiments, no beam flattening filter is arranged in the radiation path of the x-ray. The radiation path of the x-ray beam can be collimated in order to form the lateral profile.

In some embodiments, the x-ray beam, which has a maximum intensity in the central beam and which, with a medical device operating with x-rays is emitted from an x-ray source from different spatial directions about an isocenter, is used to homogenize the dose in an area around the isocenter, by the central beam of the x-ray beam being aligned laterally past the isocenter in each spatial direction.

With the aid of FIG. 1, the principle of dose generation about an isocenter in a radiation therapy device is explained according to the prior art.

The radiation therapy device 11 includes a rotatable gantry 13, with which an x-ray radiation source 15 can be rotated around the object to be irradiated. A conical x-ray beam is directed at the isocenter 19 from the x-ray radiation source. The x-ray beam is laterally delimited by a collimator 17. The irradiation usually takes place from different directions by rotating the x-ray source 15 around the isocenter 19, indicated by the positions of the gantry shown with dashed lines.

The central beam 21 of the conical x-ray beam strikes the isocenter 19 in the process. The x-ray beam in this way has a dose distribution 23, indicated by the Gaussian-type curve, which has a maximum dose along the central beam 21, which tapers toward the edge. If a target volume is irradiated with the particle beam, the dose rate in the isocenter 19 is therefore at its highest and attenuates toward the edge.

This principle is made clearly apparent by the applied dose generated by the two irradiation directions shown opposite one another. The dose maxima illuminate the target volume at the same point, so that the dose applied by the two irradiation directions in the target volume has the same inhomogeneous distribution as the inhomogeneous dose distribution 23 in the x-ray beam.

A beam flattening filter (not shown here) is therefore generally used in a radiation therapy device 11 according to the prior art, said beam flattening filter being arranged in the radiation path of the x-ray beam and rendering the inhomogeneous dose profile more homogenous. This however takes place at the cost of the radiation dose which is destroyed in the beam flattening filter.

Figure 2:
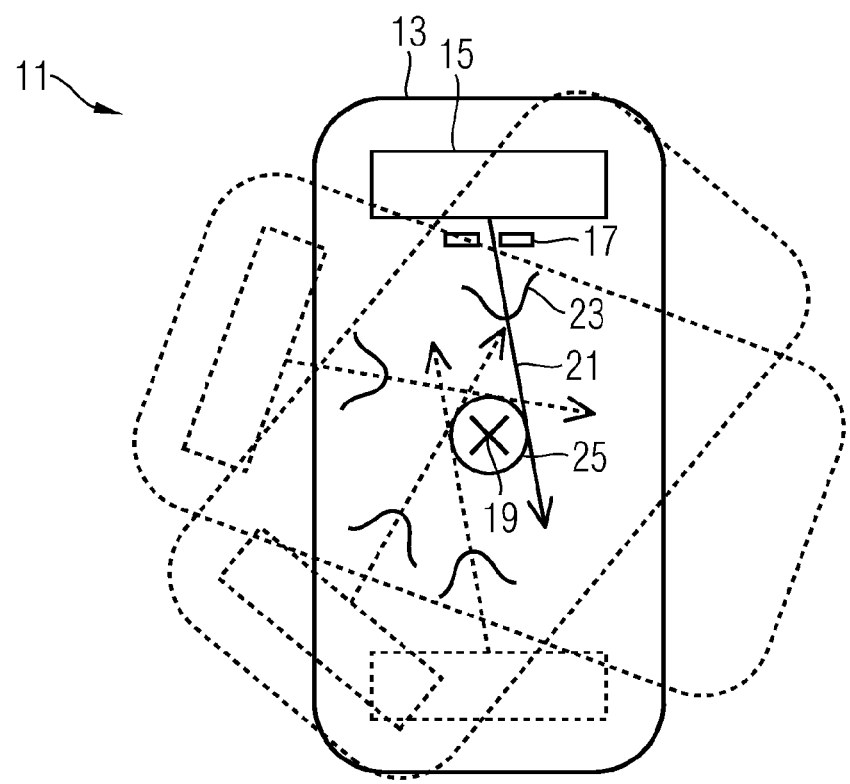
FIG. 2 shows the principle of dose generation in a radiation therapy device according to an example embodiment of the present invention.

FIG. 2 shows the principle of dose generation in an example radiation therapy device 11 according to one embodiment of the present invention.

The central beam 21 of the x-ray source 15 is now no longer aligned toward the isocenter 19, but aims paraxially past the isocenter. Upon rotation of the x-ray source 15 about the isocenter 19, this results in the central beams 21 emitted being tangential to a circle 25 around the isocenter.

The dose which is set up around the isocenter 19 in geometric configurations of this type, is clearly more homogenous compared with a dose which was applied when aligning the central beam 23 to the isocenter 19.

This is clearly apparent with the aid of the two irradiation directions shown opposite one another. The maximum dose which is applied by the respective irradiation directions is now no longer in the isocenter 19, but instead respectively at an opposite point of the isocenter 19. Dose portions which clearly lie below the maximum dose are added together in the isocenter 10 itself by the opposite irradiation. By adding the dose portions, a dose is applied in the isocenter 19, which is significantly closer to the maximum dose than the individual dose portions themselves. A significantly more homogenous dose can be applied overall as a result.

Ideally it is therefore even possible to completely dispense with a beam flattening filter. No dose output is then destroyed in the beam flattening filter, as a result of which the target volume can be illuminated with a higher dose rate, which significantly reduces irradiation time.

Provision can also be made here for a collimator 17, which adjusts and restricts the applied dose to a target volume.

Even if the principle was explained with the aid of a radiation therapy device 11, the same principle of achieving a dose homogenization of the dose distribution set up about an isocenter 13 can be transferred to imaging devices operating with x-rays, such as for instance a computed tomography system (CT) or a cone beam CT.

LIST OF REFERENCE CHARACTERS

11 Radiation therapy device
13 Gantry
15 x-ray radiation source
17 Collimator
19 Isocenter 21 Central beam
23 Dose distribution
25 Circle

What is claimed is:

1. A medical device operating with x-rays, comprising:
a rotation apparatus,
a single x-ray radiation source mounted on the rotation apparatus, the single x-ray radiation source configured to emit an x-ray radiation cone having an inhomogeneous intensity profile which has a maximum intensity along a central beam and a lower intensity away from the central beam,
wherein the rotation apparatus is configured to rotate the single x-ray radiation source about an isocenter,
wherein the single x-ray radiation source is mounted on the rotation apparatus at a fixed, non-isocentric angle relative to the rotation apparatus throughout the rotation of the x-ray radiation source about the isocenter, such that the x-ray radiation cone emitted by the single x-ray radiation source maintains a fixed angle relative to the rotation apparatus throughout the rotation of the x-ray radiation source about the isocenter,
wherein the central axis of the x-ray radiation cone is aligned paraxially past the isocenter such that for any particular rotational position of the single x-ray radiation source, the intensity of x-ray radiation at the isocenter is less than the maximum intensity along the central beam of the x-ray radiation cone,
wherein the fixed angle of the single x-ray radiation source relative to the rotation apparatus is selected such that upon rotation of the single x-ray radiation source, the central beam of the x-ray radiation cone follows a path that is tangential to an imaginary circle around the isocenter to provide a collective illumination near the isocenter that is more homogenous than the inhomogeneous intensity profile of the x-ray radiation cone.

2. The medical device of claim 1, wherein the device is embodied as a radiation therapy device.

3. The medical device of claim 1, wherein a collimator exists in the radiation path of the x-ray radiation cone for lateral delimitation of the beam profile of the x-ray beam.

4. The medical device of claim 1, wherein no beam flattening filter which is used for spatial dose homogenization is arranged in the radiation path of the x-ray radiation cone.

5. A method for operating a medical device, comprising:
providing a single x-ray radiation source mounted to a rotation apparatus, the single x-ray radiation source configured to emit an x-ray radiation cone having an inhomogeneous intensity profile which has a maximum intensity along a central beam and a lower intensity away from the central beam, and
rotating the single x-ray radiation source about an isocenter,
wherein the single x-ray radiation source is mounted on the rotation apparatus at a fixed, non-isocentric angle relative to the rotation apparatus throughout the rotation of the x-ray radiation source about the isocenter, such that the x-ray radiation cone emitted by the single x-ray radiation source maintains a fixed angle relative to the rotation apparatus throughout the rotation of the x-ray radiation source about the isocenter, and
wherein the central axis of the x-ray radiation cone is directed paraxially past the isocenter such that for any particular rotational position of the single x-ray radiation source, the intensity of x-ray radiation at the isocenter is less than the maximum intensity along the central beam of the x-ray radiation cone, and
wherein the fixed angle of the single x-ray radiation source relative to the rotation apparatus is selected such that as the single x-ray radiation source rotates around the isocenter, the central beam of the x-ray radiation cone follows a path that is tangential to an imaginary circle around the isocenter to provide a collective illumination near the isocenter that is more homogenous than the inhomogeneous intensity profile of the x-ray radiation cone.

6. The method of claim 5, wherein no beam flattening filter used for spatial dose homogenization is arranged in the radiation path of the x-ray radiation cone.

7. The method of claim 5, wherein the x-ray radiation cone is collimated.

* * * * *